United States Patent [19]

De La Fuente

[11] Patent Number: 6,160,112
[45] Date of Patent: Dec. 12, 2000

[54] PROCEDURE FOR THE PREPARATION OF DIOXOPENICILLANIC ACID DERIVATIVES

[75] Inventor: Juan Pedro Morata De La Fuente, Madrid, Spain

[73] Assignee: Alex-Gyogyszer Kutatási, Fejlesztési és Tanácsado Korlátot Felelösségu Társagag, Budapest, Hungary

[21] Appl. No.: 09/261,236

[22] Filed: Mar. 3, 1999

[51] Int. Cl.[7] .................................................. C07D 499/04
[52] U.S. Cl. ............................................................ 540/310
[58] Field of Search ............................................. 540/310

[56] References Cited

PUBLICATIONS

CA 115:8423, abstract of Esteban–Pinilla et al, ES 2,010, 485, abstract attached.
CA 121:35178, abstract of Esteban–Pinilla et al, ES 2,039, 299, abstract attached.

*Primary Examiner*—Mark L. Berch
*Assistant Examiner*—Thomas McKenzie
*Attorney, Agent, or Firm*—Evanson, McKeown, Edwards & Lenahan, P.L.L.C.

[57] ABSTRACT

Procedure for the preparation of dioxopenicillanic acid derivatives and its salts pharmaceutically acceptable with general formula I, where, R is hydrogen, alkyl group containing 1 to 5 Carbon atoms or a residue of type —CH2R', where R' is hydrogen, halogen or a p-toluensulfonyl group. These are prepared by treatment of the compounds of general formula II, where R is as previously defined and X may be hydrogen or bromine, with a metallic reagent constituted by a mixture or alloy of copper and/or cobalt and/or manganese with iron and/or nickel in an aqueous/organic medium.

These compounds are useful as inhibitors of beta-lactamase.

(I)

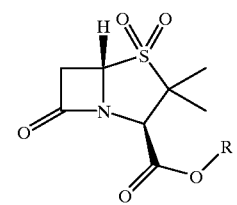

(II)

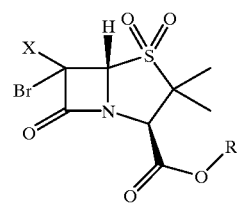

11 Claims, No Drawings

PROCEDURE FOR THE PREPARATION OF DIOXOPENICILLANIC ACID DERIVATIVES

DESCRIPTION

The invention describes a procedure for the preparation of derivatives of 1,1-dioxopenicillanic acid and its salts pharmaceutically acceptable with general formula I.

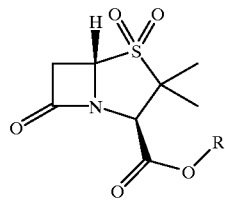
(I)

where R is hydrogen, lower alkyl or a residue of type

—$CH_2R'$ where R' is hydrogen, halogen or a p-toluensulfonyl group.

The term "lower alkyl" used herein embraces especially alkyl groups containing 1 to 5 Carbon atoms.

The products examined in this invention comprise one of the most important groups of semisynthetic inhibitors of beta-lactamase, as described by A. R. English in Antimicrob. Ag. Chemother., 14, 414 (1978).

Several clinical studies have been carried out combining this type of product with penicillanic antibiotics, particularly with Ampicillin, notably that of Campoli-Richards and Brodget published in Drugs 33, 577–6099 (1987) in which the authors review the synergetic effect of Ampicillin with Sulbactam.

The results obtained in these and several subsequent studies have led to the customary application of a combination of penicillin antibiotics with Sulbactam (R=hydrogen, Formula I) or similar products. In this way the correct proportion of antibiotic: inhibitor dosage is achieved.

The positive activity of this type of inhibitor has been shown in the development of other types of active principles in which the inhibitor/antibiotic combination is established by a chemical link such as methanodiol ester saponifiable "in Vivo" as is the case of Sultamicillin.

In this manner transportation of the inhibitor and the antibiotic is identical and as a consequence maximum efficiency of action is obtained.

Various methods have been described for the preparation of the products involved in this invention, in particular procedures involving direct oxidation of penicillanic acid obtained by deamination of 6-aminopenicillanic acid. Notably the method described in Belgian patent BE 867859 in which oxidation is carried out with alkaline permanganate.

Other procedures involve the dehalogenation of 6- halo and/or 6,6-dihalopenicillanic acids, which have been previously reduced by hydrogenation process with a Palladium carbon catalyst, the method claimed in DE 3008257. Preparation of halogenated products is carried out by means of diazotisation of 6-aminopenicillanic acid.

Variants of the latter method have also been described, namely those in which the final dehalogenation is carried out by treating the original products with Cd metal as in ES 8609339, Magnesium in European Patent EP 138282 or Zinc in EP 092286 in a neutral or weak acidic medium.

Of particular interest is the method described in patents EP 139048 and EP 138282 in which the treatment of the halogen derivative with Mg in a hydrochloride medium produces dehalogenation with an acceptable yield. The base material is obtained by means of diazotisation and subsequent halogenation of the 6-amino-1,1-dioxopenicillanic acid.

A similar method is the dehalogenation process claimed in Spanish Patent ES 8901442, where the process is carried out using powdered Iron in an aqueous organic medium.

Another system for the preparation of dioxopenicillanic acids has also been described whereby the relevant mono and dihalogenated derivatives are subjected to electrolytic reduction as described in JP 61063683.

As will be detailed below the process proposed in this document consists of the preparation of general formula compounds I, through reaction of compounds of formula II with a mixture or alloy of reductive metals

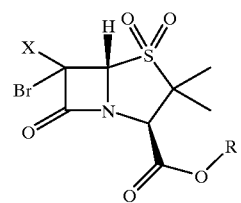
(II)

where R is as previously defined and X may be hydrogen or bromine

The use of a mixture or alloy of two or more metals such as those used in the invention described has considerably improved the purification process and mitigated reaction conditions in contrast to the procedures described in the available literature.

The following Table I shows the comparative results obtained in the tests using a single metal, Fe, as opposed to mixtures or alloys of two or more metals such as Iron, Nickel, Cobalt, Copper and Manganese. The tests were all carried out in similar conditions using a mixture of organic solvent, ethyl acetate or acetonitrile in a buffered solution with a pH ranging between 3.5 and 4.5.

TABLE 1

Tests of dehalogenation of 6,6-dibromo-1,1-dioxopenicillanic acid (II, R=Br)

| METAL | Organic Solvent | Reaction Time (hours) | Conversion (%) | Yield (%) |
|---|---|---|---|---|
| Iron | Ethyl acetate | 4.5 | 83 | 80 |
| Fe + Ni (4;5) | " | 4.5 | 78 | 49 |
| Cu + Mn (1:1) | " | 6 | 75 | 37 |
| Fe + Mn (7:3) | " | 6.5 | 87 | 82 |
| Fe + Co (7:3) | " | 6 | 90 | 85 |
| Ni + Cu (9:1) | Acetonitrile | 3.5 | 90 | 84 |
| Ni + Cu (7:3) | " | 3 | 91 | 86 |
| Co + Cu + Fe (4:4:2) | " | 4.5 | 85 | 75 |
| Fe + Co + Cu (7.5:1.5:1) | Ethyl Acetate | 2.5 | 97 | 92 |
| Ni + Fe + Cu (5:5:1.5) | " | 3.5 | 90 | 84 |
| Fe + Co + Cu (997:2:1) | " | 2 | 97 | 91.5 |

Pure Fe was selected as a basis for comparison as, according to the available literature, the best results have been obtained using this metal.

Detailed analysis of the results obtained revealed the following conclusions. In the alloys of Iron and other metals, excluding Nickel, the resulting reaction rises as the proportion of these metals increases using Iron as a base.

Notwithstanding there is a maximum point from which an increase in the proportion of these metals causes a marked descent in yield of reaction over a given time.

Results obtained with mixtures and/or alloys of Nickel with other metals confirm a similar behavior to that of Iron.

Tests carried out show that dehalogenation is more efficiently produced with a mixture or alloy of Iron or Nickel with Cobalt than with Copper or Manganese. However the best results were obtained with mixtures or alloys of Iron or Nickel used simultaneously with other metals and with each other.

It should be noted, with regard to the combination of metals, that physical mixtures and alloys of an approximately equal composition behaved in the same manner with no significant variations in yield or purity of the final product.

On a practical level it has also been shown that the use of this mixture or alloy of various metals, whilst increasing yield, generates fewer secondary products, thus providing a much simpler purification process.

In certain conditions, by merely eliminating the aqueous and filtration phase following solvent evaporation, an extremely pure final product is produced.

Also, the almost total absence of impurities in the products thus obtained has facilitated the preparation of alkaline salts of 1,1-dioxopenicillanic acid (compound I, R=H) in the form of highly crystalline products.

The resulting products are both extremely pure and highly stable showing no signs of degradation even after long periods of time under harsh conditions.

The high crystallinity of the salts also means considerable improvements in their properties, facilitating their subsequent formulation. Thus they show less hygroscopicity, greater powder fluidity and ease in mixing with other products which make them particularly useful in the preparation of injectable substances.

The procedure shows therefore, an important advance in view of the disclosures described in the currently available literature.

Thus in comparison with the required instrumental complications of more complex processes such as catalytic hydrogenation, the advantages of working with metals is indicated in the low cost and simple reaction conditions.

Moreover compared to the methods described in the available literature on the use of metals, this invention provides a significant increase in yields without raising costs and with obvious advantages in terms of reaction times and purification procedures of the final product. This has been sufficiently demonstrated by the results shown in the table I.

The procedure basically involves the preparation of compounds of general formula I and its salts by treatment of compounds of general formula II with a mixture or alloy of reductive metals in an aqueous/organic medium.

The metal reagent is a mixture or alloy of Copper and/or Cobalt and/or Manganese with Iron and/or Nickel. The composition of this mixture or alloy is widely varied.

When alloys or mixtures of Iron with other metals excepting Nickel are used, the best results are obtained if the percentage of Iron is greater than 50%. In these cases the percentage of at least one of the other metals is understood to be within the range of 0.05% to 40%.

When alloys or mixtures of Nickel with other metals are used excepting Iron, the best results are obtained if the percentage of Nickel is greater than 50%. In such cases the percentage of at least one of the other metals is understood to be between 0.05% to 40%.

In the case of alloys and mixtures which contain both Iron and Nickel the best results are obtained when the percentages of both are similar, and together greater than 80%. In these cases the percentage of at least one of the other metals is understood to be between 0.05% to 20%.

The composition of the dehalogenating reagent, which produced the best results, includes the following values, for Iron 75 to 90%, for Cobalt 10 to 15% and for Copper 5 to 10%. With a similar composition, but substituting Iron for Nickel, slightly lower yields were obtained.

The solvent used was a mixture of water and a polar organic solvent such as Ethyl ether, Ethyl acetate, Acetonitrile, Methyl acetate or similar. The best results were obtained with Ethyl acetate.

Although temperature does not have a significant influence on the development of the reaction, tests were carried out with temperatures ranging from 10 to 30° C. Temperature increases above these figures did not lead to improved results.

Conversely pH was seen to be an important factor. The reaction led to good results with a pH ranging between 2 and 6. The best results were obtained from a pH ranging between 3.5 and 5.

When the reaction was over, in most cases, isolation and purification were relatively simple given the almost total absence of secondary or degraded products. In these cases preparation of the final compounds was carried out using the customary methods.

Some examples are provided below, which together with the results indicated in Table 1, help to indicate the scope of the invention.

EXAMPLE 1

1,1-Dioxopenicillanc Acid

Over a mixture of:

40 g of 6,6 dibromo-1,1-dioxopenicillanic acid 220 ml of ethyl acetate 80 ml of water a solution of:

10 g of sodium acetate was added together with 30 ml of glacial acetic acid 20 ml of water was added.

The mixture was shaken for ten minutes at room temperature and a homogenous mixture of:

15 g of Iron 1.0 g of Cobalt 2.0 g of Copper in fine powder form was added.

This temperature was maintained and the mixture shaken for 2.5 hours and then filtered.

The organic layer was decanted and washed with:

200 ml of brine, and 100 ml of water it was dried on sodium sulphate, filtered and evaporated to obtain:

22.0 g of the title compound as a white slightly cream coloured solid (92% yield).

Spectroscopic Data

IR (KBr) vmax. 2650–3350, 1780, 1740 cm−1

$^1$H RMN (DMSO) 1.40 (s), 1.50 (s), 3.60 (dd), 4.30 (s) 5.10 (d) ppm

EXAMPLE 2

Dehalogenation of the 6-bromo-1,1-dioxopenicillanic acid according to the procedure of Example 1, affords the same result.

EXAMPLE 3

Methyl 1,1-dioxopenicillanate

Over a solution of:
- 20.2 g of methyl 6,6-dibromo-1,1-dioxopenicillanate
- 100 ml of acetonitrile
- 50 ml of water:

previously cooled to 10° C., a solution of:
- 10 g of Monosodium phosphate
- 10 ml of Phosphoric acid
- 50 ml of water was added, while maintaining the temperature below 15° C.

The mixture was shaken for 10 minutes and a mixture of
- 10 g of Iron
- 10 g of Nickel
- 3.0 g of oxide free Copper in the form of powder was added.

Agitation was continued at a temperature between 10 an 15° C. for 4 hours and the mixture was then filtered and the organic solvent was evaporated under vacuum.

150 ml of dichloromethane was added and the organic layer was decanted and washed with:
- 120 ml of brine, and
- 50 ml of water It was dried over sodium sulphate and evaporated. The residue was dissolved in the minimum quantity possible of ethyl acetate and, stirring vigorously, petroleum ether was added drop by drop until turbidity.

Agitation was maintained overnight and the solid was then filtered and dried under vacuum to yield:
- 10.8 g of the title compound as a light cream solid (88% yield)

Spectroscopic Data
  IR (KBr) vmax. 1800, 1740, 1320 cm−1
  $^1$H RMN (DMSO) 1.40 (s), 1.50 (s), 3.25 (d), 3.60 (m), 3.70 (s), 4.35 (s), 5.20 (d) ppm

EXAMPLE 4

Chloromethyl 1,1-dioxopenicillanate

Over a solution of:
- 16.0 g. of chloromethyl 6,6 dibromo-1,1-dioxopenicillanate and
- 160 ml of ethyl acetate/water (1:1)

a metallic alloy containing:
- 1.5 g of Cobalt
- 1.1 g of powdered Manganese
- 10 g of powdered Iron was added.

The mixture was agitated at room temperature for 30 minutes and 15 ml of glacial acetic acid was added.

Stirring continued for a further two hours and the mixture was then filtered.

The organic layer was decanted and washed with
- 50 ml of water

It was then dried and filtered and the solvent was evaporated. The residue was macerated for a night with n-pentane and subsequently filtered and dried under vacuum to yield:
- 8.3 g of the title compound in the form of a white solid (81.5% yield)

Spectroscopic Data
  IR (KBr) vmax. 1800, 1750, 650 cm−1

EXAMPLE 5

1,1-Dioxopenicillanic Acid

Over a mixture of:
- 40 g of 6,6 dibromo-1,1 dioxopenicillanic acid
- 200 ml of acetonitrile
- 70 ml of water a solution of:
- 10 ml of glacial acetic acid
- 50 ml of water was added.

The mixture was shaken for ten minutes at room temperature and a homogenous mixture of:
- 9.0 g of Nickel
- 1.0 g of Copper in fine powder form was added.

This temperature was maintained and the mixture shaken for 2.5 hours and then filtered.

The organic layer was decanted and washed with:
- 300 ml of dichloromethane
- 200 ml of brine, and
- 100 ml of water The organic layer was decanted and it was dried on sodium sulphate, filtered and evaporated to obtain:
- 20.0 g of the title compound as a white slightly cream coloured solid (84% yield).

Spectroscopic Data
  IR (KBr) vmax. 2650–3350, 1780, 1740 cm−1
  $^1$ H RMN (DMSO) 1.40 (s), 1.50 (s), 3.60 (dd), 4.30 (s) 5.10 (d) ppm

EXAMPLE 6

Dehalogenation of the 6,6-dibromo-1,1-dioxopenicillanic and 6-bromo-1,1-dioxopenicillanic acid, according to the procedure of Example 5 using an alloy of the same metals and composition as the mixture of Example 5 instead it, affords the same results.

EXAMPLE 7

1,1-Dioxopenicillanic Acid

Over a mixture of:
- 20 g of 6-bromo-1,1-dioxopenicillanic acid
- 150 ml of methyl acetate
- 50 ml of water a solution of:
- 5 ml of phosphoric acid
- 50 ml of water was added.

mixture of:
- 7 g of Iron
- 3.0 g of Manganese in fine powder form was added.

The mixture was shaken for 2.5 hours and then filtered.

The organic layer was decanted and washed with:
- 150 ml of brine, and
- 100 ml of water it was dried on sodium sulphate, filtered and evaporated to obtain:
- 12.2 g of the title compound as a solid (80% yield).

EXAMPLE 8

Methyl 1,1-Dioxopenicillanate

Over a solution of:
- 10.8 g of methyl 6,6-dibromo-1,1-dioxopenicillanate 200 ml of ethyl acetate 20 ml of water:

previously cooled to 5° C., a solution of:

20 ml of 10% aqueous acetic acid was added, while maintaining the temperature below 15° C. The mixture was shaken for 10 minutes and a metallic alloy containing:

9 g of Nickel 0.5 g of Cobalt 0.5 g of Manganese in the form of powder was added.

Agitation was continued at a temperature between 10 an 15° C. for 4 hours and the mixture was then filtered and the organic solvent was evaporated under vacuum.

150 ml of dichloromethane was added and the organic layer was decanted and washed with:

120 ml of brine, and 50 ml of water

It was dried over sodium sulphate and evaporated. The residue was dissolved in the minimum quantity possible of ethyl acetate and, stirring vigorously, petroleum ether was added drop by drop until turbidity.

Agitation was maintained overnight and the solid was then filtered and dried under vacuum to yield:

5.54 g of the title compound as a solid (84.5% yield)

What is claimed is:

1. A method for preparing a 1,1-dioxopenicillanic acid compound corresponding to formula I:

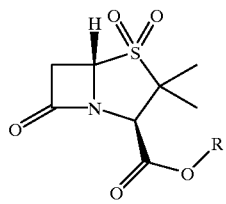

(I)

wherein

R represents hydrogen, an alkyl group containing 1 to 5 carbon atoms or a group corresponding to the formula:

CH$_2$R' wherein R' represents hydrogen, halogen or p-toluensulfonyl; said method comprising:

treating a compound corresponding to formula II:

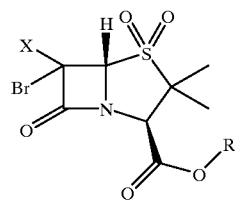

(II)

wherein R is as defined above and X is hydrogen or bromine with a metallic dehalogenating reagent consisting of a mixture or alloy of at least one metal selected from the group consisting of copper, cobalt and manganese, with at least one metal selected from the group consisting of iron and nickel in an aqueous organic medium.

2. A method according to claim 1, wherein said metallic dehalogenating reagent is composed of a mixture or alloy of cobalt and copper with nickel, said mixture or alloy comprising from 0.05% to 40% cobalt and from 0.05% to 40% copper.

3. A method according to claim 2, wherein said mixture or alloy comprises from 10% to 15% cobalt and from 5% to 10% copper.

4. A method according to claim 1, wherein said metallic dehalogenating reagent is composed of a mixture or alloy of cobalt and copper with iron; said mixture or alloy comprising from 0.05% to 40% cobalt and from 0.05% to 40% copper.

5. A method according to claim 4, wherein said mixture or alloy comprises from 10% to 15% cobalt and from 5% to 10% copper.

6. A method according to claim 1, wherein said metallic dehalogenating reagent comprises a mixture or alloy of 30% nickel, 65% iron and 5% cobalt.

7. A method according to claim 1, wherein the pH is maintained between 2 and 6.

8. A method according to claim 7, wherein the pH is maintained between 3.5 and 5.

9. A method according to claim 1, wherein X represents bromine and R represents hydrogen.

10. A method according to claim 1, wherein X represents bromine and R represents methyl.

11. A method according to claim 1, wherein X represents bromine and R represents a —CH$_2$R' group, wherein R' is an atom of chlorine.

* * * * *